(12) United States Patent
Montemurro et al.

(10) Patent No.: US 10,451,526 B2
(45) Date of Patent: Oct. 22, 2019

(54) METHOD AND SYSTEM FOR SENSOR MONITORING AND ANALYSIS

(71) Applicant: BlackBerry Limited, Waterloo (CA)

(72) Inventors: Michael Peter Montemurro, Toronto (CA); Roland Emlyn Williams, San Ramon, CA (US); James Randolph Winter Lepp, Ottawa (CA); Stephen McCann, Southampton (GB)

(73) Assignee: BlackBerry Limited, Waterloo, Ontario (CA)

( * ) Notice: Subject to any disclaimer, the term of this patent is extended or adjusted under 35 U.S.C. 154(b) by 149 days.

(21) Appl. No.: 15/664,024

(22) Filed: Jul. 31, 2017

(65) Prior Publication Data

US 2019/0033172 A1  Jan. 31, 2019

(51) Int. Cl.
| | | |
|---|---|---|
| *G06F 19/00* | (2018.01) | |
| *G01M 17/013* | (2006.01) | |
| *G01M 17/02* | (2006.01) | |
| *G06K 9/00* | (2006.01) | |
| *H04L 29/08* | (2006.01) | |

(52) U.S. Cl.
CPC ........ *G01M 17/013* (2013.01); *G01M 17/025* (2013.01); *G06K 9/00798* (2013.01); *H04L 67/12* (2013.01)

(58) Field of Classification Search
CPC ........ G07C 5/008; H04L 67/12; G05B 13/028
USPC .......................... 702/182, 183, 184, 185, 188
See application file for complete search history.

(56) References Cited

U.S. PATENT DOCUMENTS

| | | |
|---|---|---|
| 7,089,099 B2 | 8/2006 | Shostak et al. |
| 2004/0017289 A1 | 1/2004 | Brown, Jr. |
| 2005/0194497 A1 | 9/2005 | Matzan |
| 2006/0145881 A1 | 6/2006 | Sakatani et al. |
| 2007/0156320 A1 | 7/2007 | Breed et al. |
| 2010/0161255 A1 | 6/2010 | Mian et al. |
| 2014/0070935 A1 | 3/2014 | Wang et al. |
| 2014/0257621 A1 | 9/2014 | Zych |
| 2016/0009290 A1 | 1/2016 | Benedict et al. |

FOREIGN PATENT DOCUMENTS

WO   2015071081   5/2015

OTHER PUBLICATIONS

Mary Wilson, "Real time Trailer Monitoring System", https://web.archive.org/web/20140203080329/http://circuitcellar.com/cc-blog/real-time-trailer-monitoring-system/, Dec. 16, 2013.

International Search Report arid Written Opinion of the International Searching Authority issued in international Application No. PCT/US2018/44474 dated Oct. 16, 2018; 8 pages.

*Primary Examiner* — Edward Raymond

(74) *Attorney, Agent, or Firm* — Fish & Richardson P.C.

(57) ABSTRACT

A method for monitoring performance of at least one component on a moving platform, the method including receiving sensor data for the at least one component, along with supplemental data, at a processing node; and processing the sensor data, the processing using the supplemental data to filter the sensor data.

21 Claims, 6 Drawing Sheets

METHOD AND SYSTEM FOR SENSOR MONITORING AND ANALYSIS

FIELD OF THE DISCLOSURE

The present disclosure relates to sensor systems and in particular relates to sensor systems for tire and bearing monitoring on a transport trailer.

BACKGROUND

An important area for the maintenance of a fleet of transportation vehicles involves tire and wheel bearings within vehicles. This is particularly true of trailers, since such trailers are generally equipped with less sophisticated sensors from an electronics point of view.

In today's systems, inspection and maintenance of tires and wheel bearings is done manually at regular intervals. The intervals could be based on a combination of mileage and time. However, manual inspection of tires and wheel bearings may depend on the skill of the operator and may be error prone. Furthermore, the inspection typically occurs when the trailer or vehicle is stationary and therefore is merely a snapshot of the condition of the tire and wheel bearings. This may cause errors, especially when components are not easily visible and there is generally no indication of impending failure.

Rotating components such as tires and wheel bearings (bearings) perform under significant stress, and are generally overdesigned so that catastrophic failure is mitigated. However, even with such considerations, economic pressures tend to cause some lower integrity components to be installed. For example, a tire carcass that comprises a loadbearing component such as the bead and chords is often "recapped" or "retreaded" after a thorough cleaning and inspection of the carcass condition. However, unlike a new tire, a cap component has a lower integrity and it is not uncommon for separation or delamination to occur, resulting in overheating and destructive shedding of some or all of the tire.

While tire pressure monitoring systems (TPMS) allow an operator to monitor tire pressures in a vehicle, such TPMS systems only provide alarms after a tire suddenly loses pressure or blows. This does not deal with bearing degradation or tire delamination issues.

BRIEF DESCRIPTION OF THE DRAWINGS

The present disclosure will be better understood with reference to the drawings, in which.

DETAILED DESCRIPTION OF THE DRAWINGS

Figure 1:
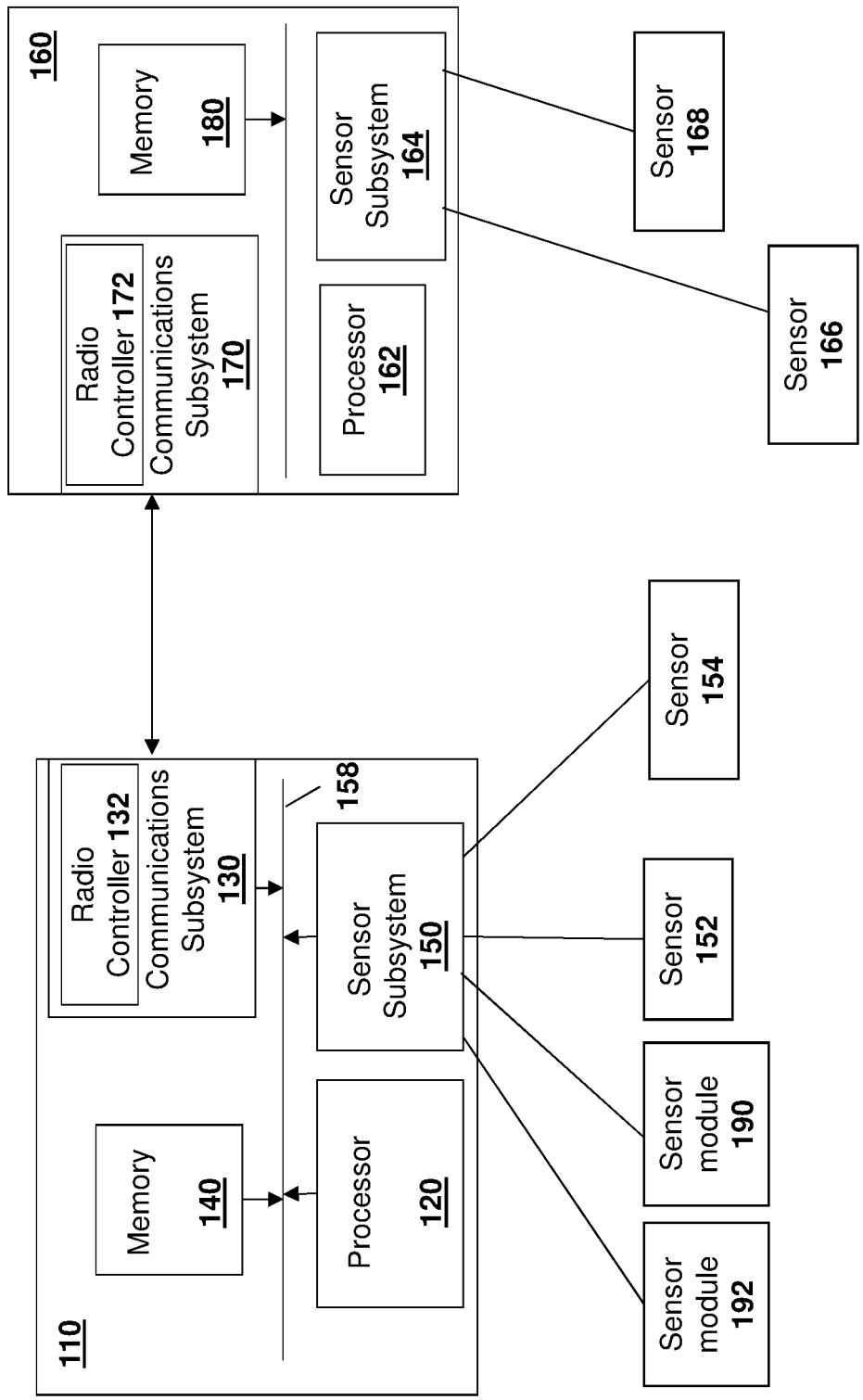
FIG. 1 is a block diagram showing an example gateway and sensor module capable of being used in accordance with the embodiments of the present disclosure.

The present disclosure provides a method for monitoring performance of at least one component on a moving platform, the method comprising: receiving sensor data for the at least one component, along with supplemental data, at a processing node; and processing the sensor data, the processing using the supplemental data to filter the sensor data.

The present disclosure further provides a processing node for monitoring performance of at least one component on a moving platform, the processing node comprising: a processor; and a communications subsystem, wherein the processing node is configured to: receive sensor data for the at least one component, along with supplemental data; and process the sensor data, the processing using the supplemental data to filter the sensor data.

The present disclosure further provides a computer readable medium for storing instruction code, which, when executed by a processor on a processing node are configured for monitoring performance of at least one component on a moving platform, the instruction code causing the processing node to: receive sensor data for the at least one component, along with supplemental data; and process the sensor data, the processing using the supplemental data to filter the sensor data.

In accordance with one embodiment of the present disclosure, inspection and maintenance for rolling components such as tires and bearings is augmented by developing a sensor network to monitor bearing conditions, including temperature and vibration, wheel assembly vibration, as well as tire pressure and temperature. The results of such monitoring may be aggregated and the data processed to alert an operator and/or a fleet manager when inspection and maintenance is required.

The present disclosure is provided below with regard to a trailer. However, in other embodiments other vehicles or equipment could equally benefit from the disclosure provided herein. Therefore, the use of the sensors on the trailer is merely provided as an example.

In accordance with the embodiments of the disclosure provided below, a sensor system is provided on a trailer. Such a sensor system may include, but is not limited to, wheel bearing sensors that may include temperature sensors and accelerometers, tire pressure monitoring sensors, and/or acoustic sensors. Such sensors may record readings of tire, bearing and wheel assembly data at pre-determined intervals. For example, the readings may be taken every five minutes in some embodiments.

The sensor data, including temperature information, acceleration or vibration information, acoustic information among other data, could be sent to a wireless gateway associated with the sensor system.

The wireless gateway may periodically upload the sensor data to a cloud or server. The uploading may occur in various manners. For example, in a first embodiment, raw data may be uploaded at regular intervals. In other embodiments security and/or compression could be applied to the data. In still further embodiments, raw data may be collected and uploaded only after a trip has finished. In some cases, the raw data may be processed at the sensor system, and any anomalous behavior may trigger an alarm immediately. Other examples for data uploading are possible.

In addition to the above sensors, a micro-electromechanical (MEMS) sensor may be used to detect out of balance components and may alert a system to impending failure, for example due to partial separation or delamination of the tread of the tire.

Further, accelerometer data may contain acoustic information. Although this appears as noise in the acceleration spectrum relevant to the wheel frequencies, such information may comprise higher frequency components which are representative of tire noise over the road as well as bearing noise. This information may be extracted, for example using the Fast Fourier Transform, and the spectral data may be used to monitor a change in the condition of the rotating assembly well in advance of catastrophic failure.

For example, the data may indicate that a simple wheel change will alleviate an impending tire failure from increased imbalance. Since bearing performance is directly affected by offset loads due to imbalance, an early remedy may result in greatly reduced wear and subsequent maintenance downtime.

Also, bearings are known to exhibit acoustic noise in the ultrasonic acoustic range as part of normal operations and this may be detected by an accelerometer or other microphonic techniques.

In further embodiments, other sensors may also be incorporated into the system. For example, strain gauges or sensors that monitor brake wear could be used. Brake wear sensors may issue warnings when brakes are worn below a safe minimum or worn unevenly, and provide an indication as to when brakes may require maintenance.

In other cases, supplemental data such as position/location fixes, visual cues, environmental temperature, pressure or other readings may be used in conjunction with the bearing and tire sensors. The use of such supplemental data can be used to filter results and enhance the prediction of component wear and potential failure.

The above is implemented on a vehicle or trailer using a sensor system. One sensor system is shown with regard to FIG. 1. The sensor system of FIG. 1 is however merely an example and other sensor systems could equally be used in accordance with the embodiments of the present disclosure.

Reference is now made to FIG. 1, which shows an example sensor system. The sensor system of FIG. 1 includes a gateway 110, which can be any computing device or network node. In some embodiments, gateway 110 may also be referred to as a hub. Such a computing device or network node may include any type of electronic device, including but not limited to, mobile devices such as smartphones or cellular telephones. Examples can further include fixed or mobile devices, such as Internet of Things (IOT) devices, endpoints, home automation devices, medical equipment in hospital or home environments, inventory tracking devices, environmental monitoring devices, energy management devices, infrastructure management devices, vehicles or devices for vehicles, fixed electronic devices, among others.

Gateway 110 comprises a processor 120 and at least one communications subsystem 130, where the processor 120 and communications subsystem 130 cooperate to perform the methods of the embodiments described herein. The communications subsystem 130 may, in some embodiments, comprise multiple subsystems, for example different radio technologies.

The communications subsystem 130 allows gateway 110 to communicate with other devices or network elements. The communications subsystem 130 may use one or more of a variety of communications types, including but not limited to cellular, satellite, Bluetooth™, Bluetooth™ Low Energy (BLE), Wi-Fi, wireless local area network (WLAN), wireless personal area networks (WPAN), near field communications (NFC), ZigBee or any other IEEE 802.15 low power technology, wired connections such as Ethernet or fiber, among other options.

As such, a communications subsystem 130 for wireless communications will typically have one or more receivers and transmitters, as well as associated components such as one or more antenna elements, local oscillators (LOs), and may include a processing module such as a digital signal processor (DSP). As will be apparent to those skilled in the field of communications, the particular design of the communication subsystem 130 will be dependent upon the communication network or communication technology on which the sensor apparatus is intended to operate.

One or more of the radios within the communications subsystem 130 may include a radio controller 132. Such a radio controller can operate to determine if a radio within the communications subsystem 130 is receiving signals that need to be processed in one embodiment. For example, the radio controller 132 can detect if BLE communications from another component of the sensor system are trying to communicate with the gateway 110.

The processor 120 generally controls the overall operation of the gateway 110 and is configured to execute programmable logic, which may be stored, along with data, using memory 140. Memory 140 can be any tangible, non-transitory computer readable storage medium, including but not limited to optical (e.g., CD, DVD, etc.), magnetic (e.g., tape), flash drive, hard drive, or other memory known in the art. In one embodiment, the processor function may be implemented entirely in hardware, for example using a gate array, without any necessarily alterable control instructions stored in memory. This has the advantage that operation may be significantly faster than a software or firmware controlled implementation.

Alternatively, or in addition to memory 140, gateway 110 may access data or programmable logic from an external storage medium, for example through the communications subsystem 130.

In the embodiment of FIG. 1, gateway 110 may utilize a plurality of sensors to which it is coupled, which may either be part of gateway 110 in some embodiments or may communicate with gateway 110 in other embodiments. For internal sensors, processor 120 may receive input from a sensor subsystem 150.

For external sensors, sensors 152 and 154 are shown in the embodiment of FIG. 1.

Examples of sensors include, but are not limited to, a positioning sensor, a vibration sensor, a temperature sensor, one or more image sensors, accelerometer, light sensors, gyroscopic sensors, acoustic sensors, or other sensors. Other sensors may be any sensor that is capable of reading or obtaining data that may be useful for gateway 110. However, such list of sensors is merely provided as an example, and in other embodiments different sensors or a subset of sensors may be used.

In other embodiments, gateway 110 may not have any sensors, either internal or external, connected directly to it. For example, in some embodiments, gateway 110 may instead be coupled to the sensors and communicate with sensor modules, as described below.

In one embodiment, the gateway may read the sensors. For example, gateway 110 may send a page or trigger to a sensor 152 and receive a response in return.

In other embodiments, sensor 152 may communicate with gateway 110 without a page or other message.

Further, in some embodiments, sensor 152 may be capable of autonomously generating a request with gateway 110 based on a detection at the sensor of an alarm condition or out-of-bounds condition. In a sensor system, such sensor autonomy may be useful to present an alert condition that can be serviced by the gateway 110.

Communications between the various elements of gateway 110 may be through an internal bus 158 in one embodiment. However, other forms of communication are possible.

A sensor system may further include one or more sensor modules. A sensor module is a system that allows communication from various sensors, where data can be received, stored, compiled, and/or processed prior to being passed to another element in the system, such as gateway 110.

For example, in the embodiment of FIG. 1, a sensor module 160 is shown. The sensor module 160 comprises a processor 162 and at least one communications subsystem 170, where the processor 162 and communications subsystem 172 cooperate to perform the methods of the embodiments described herein. The communications subsystem 170 may, in some embodiments, comprise multiple subsystems, for example different radio technologies.

The sensor module of FIG. 1 is however merely an example, and in other embodiments may have a different configuration.

The communications subsystem 170 allows the sensor module 160 to communicate with other devices or network elements. The Communications subsystem 170 may use one or more of a variety of communications types, but would typically use short range communication such as, but not limited to Bluetooth™, BLE, Wi-Fi, WLAN, WPAN, NFC, ZigBee or other IEEE 802.15 low power technology, or wired connections such as Ethernet or fiber, among other options.

As with the communications subsystem 130, the communications subsystem 170 will typically have one or more receivers and transmitters, as well as associated components such as one or more antenna elements, local oscillators (LOs), and may include a processing module such as a digital signal processor (DSP). Again, the particular design of the communication subsystem 170 will be dependent upon the communication network or communication technology on which the sensor module is intended to operate.

One or more of the radios within the communications subsystem 170 may include a radio controller 172. Such a radio controller can operate to determine if a radio within the communications subsystem 170 is receiving signals that need to be processed in one embodiment. For example, radio controller 172 can detect if BLE communications from another component of the sensor system is being used to try to communicate with the sensor module 160.

Processor 162 generally controls the overall operation of the sensor module 160 and is configured to execute programmable logic, which may be stored, along with data, using memory 180. Memory 180 can be any tangible, non-transitory computer readable storage medium, including but not limited to optical (e.g., CD, DVD, etc.), magnetic (e.g., tape), flash drive, hard drive, or other memory known in the art. In one embodiment, processor 162 may also be implemented entirely in hardware and not require any stored program to execute logic functions.

Alternatively, or in addition to memory 180, the sensor module 160 may access data or programmable logic from an external storage medium, for example through communications subsystem 170.

In the embodiment of FIG. 1, sensor module 160 may utilize a plurality of sensors, which may either be part of sensor module 160 in some embodiments or may communicate with sensor module 160 in other embodiments. For internal sensors, processor 162 may receive input from a sensor subsystem 164.

For external sensors, sensors 166 and 168 are shown in the embodiment of FIG. 1.

In one embodiment, the sensor module 160 may read the sensors. For example, sensor module 160 may send a page to a sensor 166 and receive a response in return.

In other embodiments, sensor 166 may communicate with sensor module 160 without a page or other message.

Further, in some embodiments, sensor 166 may be capable of autonomously generating a request with sensor module 160 based on a detection at the sensor of an alarm condition or out-of-bounds condition. In a sensor system, such sensor autonomy may be useful to present an alert condition that can be serviced by sensor module 160 and/or the gateway 110.

Gateway 110 may communicate with zero, one, or a plurality of sensor modules. In the example of FIG. 1, in addition to sensor module 160, gateway 110 communicates with sensor modules 190 and 192.

In a sensor system, typically the gateway 110 will communicate with external network resources, while sensor module 160 will typically communicate internally, for example with the gateway 110, other sensor modules, or sensors.

The sensor system, including gateway 110, may be affixed to any fixed or moving platform. For example, gateway 110 may be affixed to shipping containers, truck trailers, truck cabs in one embodiment. In other embodiments, gateway 110 may be affixed to any vehicle, including motor vehicles (e.g., automobiles, cars, trucks, buses, motorcycles, etc.), aircraft (e.g., airplanes, unmanned aerial vehicles, unmanned aircraft systems, drones, helicopters, balloons, etc.), spacecraft (e.g., spaceplanes, space shuttles, space capsules, space stations, satellites, etc.), watercraft (e.g., ships, boats, hovercraft, submarines, etc.), railed vehicles (e.g., trains and trams, etc.), pedestrians and bicycles and other types of vehicles including any combinations of any of the foregoing, whether currently existing or after arising, among others. As used herein, a vehicle, container, trailer or cab may all be referred to as a moving platform.

In other cases, the gateway 110 could be carried by a user.

In other cases, the gateway 110 may be affixed to stationary objects including buildings, lamp posts, fences, cranes, temporary fixtures such as emergency shelters and tents, among other options.

Such a sensor system, and specifically the gateway 110, sensor modules 160, 190 or 192, or sensors 152, 154, 166 or 168 may be power limited devices. For example, gateway 110 could be a battery-operated device that can be affixed to a shipping container or trailer in some embodiments. Other limited power sources could include any limited power supply, such as a small generator or dynamo, a fuel cell, solar power, amongst other options.

In other embodiments, components of the sensor system including gateway 110 may utilize external power, for example from the engine of a tractor pulling the trailer, from a land power source for example on a plugged in recreational vehicle or from a building power supply, among other options.

External power may further allow for recharging of energy storage systems such as batteries to allow the sensor system components such as gateway 110 to then operate in a power limited mode again. Recharging methods may also include other power sources, such as, but not limited to, solar, electromagnetic, acoustic or vibration charging.

The sensor system from FIG. 1 may be used in a variety of environments. One example environment in which the sensor system may be used is shown with regard to FIG. 2.

Figure 2:
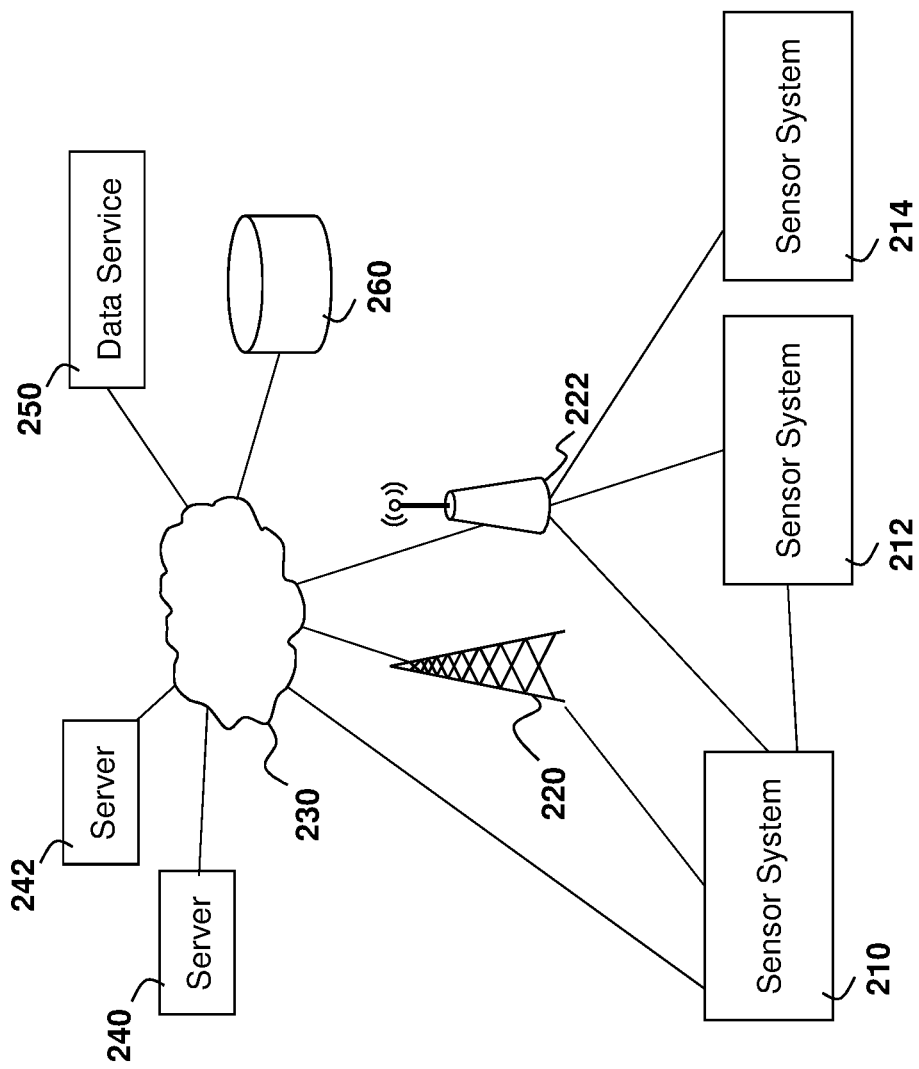
FIG. 2 is a block diagram showing an example environment for a gateway and sensor apparatus in accordance with the embodiments of the present disclosure.

Referring to FIG. 2, three sensor systems, namely sensor system 210, sensor system 212, and sensor system 214 are provided.

In the example of FIG. 2, the sensor system 210 may communicate through a cellular base station 220 or through an access point 222. The access point 222 may be any wireless communication access point.

Further, in some embodiments, the sensor system 210 could communicate through a wired access point such as Ethernet or fiber, among other options.

The communication may then proceed over a wide area network such as an internet 230 and proceed to servers 240 or 242.

Similarly, the sensor system 212 and sensor system 214 may communicate with servers 240 or server 242 through one or both of the base station 220 or access point 222, among other options for such communication.

In other embodiments, any one of sensor systems 210, 212 or 214 may communicate through satellite communication technology. This, for example, may be useful if the sensor system is travelling to areas that are outside of cellular coverage or access point coverage.

In other embodiments, the sensor system 212 may be out of range of the access point 222, and may communicate with the sensor system 210 to allow sensor system 210 to act as a relay for communications.

Communication between the sensor system 210 and server 240 may be unidirectional or bidirectional. Thus, in one embodiment the sensor system 210 may provide information to server 240 but server 240 does not respond. In other cases, server 240 may issue commands to the sensor system 210 but data may be stored internally on sensor system 210 until the sensor system arrives at a particular location. In other cases, two-way communication may exist between the sensor system 210 and server 240.

A server, central server, processing service, endpoint, Uniform Resource Identifier (URI), Uniform Resource Locator (URL), back-end, and/or processing system may be used interchangeably in the descriptions herein. The server functionality typically represents data processing/reporting that are not closely tied to the location of the sensor systems 210, 212, 214, etc. For example, the server may be located essentially anywhere so long as it has network access to communicate with the sensor systems 210, 212, 214, etc.

Server 240 may, for example, be a fleet management centralized monitoring station. In this case, server 240 may receive information from sensor systems associated with various trailers or cargo containers, providing information such as the location/position of such cargo containers, the temperature within such cargo containers, any unusual events including sudden decelerations, temperature warnings when the temperature is either too high or too low, wheel bearing and tire information, among other data. The server 240 may compile such information and store it for future reference. It may further alert an operator. For example, a sudden deceleration event may indicate that a trailer may have been in an accident and the operator may need to call emergency services and potentially dispatch another tractor to the location/position.

In other embodiments, server 240 may be a trailer tracking and maintenance server which is used to determine how far a trailer has traveled and whether any parts of the trailer need to be maintained. Maintenance may be scheduled on a time in use basis as well as other measured references, such as distance; for example lubrication may be specified in hours of use or calendar time between replacement or replenishment.

Other examples of functionality for server 240 are possible.

In the embodiment of FIG. 2, servers 240 and 242 may further have access to third-party information or information from other servers within the network. For example, a data services provider 250 may provide information to the server 240. Similarly, a data repository or database 260 may also provide information to the server 240.

For example, the data services provider 250 may be a subscription based service used by the server 240 to obtain current or historic road and weather conditions.

The data repository or database 260 may for example provide information such as image data associated with a particular location, aerial maps, detailed street maps, road surface information, or other such information.

The types of information provided by the data service provider 250 or the data repository or database 260 is not limited to the above examples and the information provided could be any data useful to the server 240.

In some embodiments, information from the data service provider 250 or the data repository from database 260 can be provided to one or more of the sensor systems 210, 212, or 214 for processing at those sensor systems.

Utilizing a sensor system such as that described above, in accordance with the various embodiments of the present disclosure, tire, wheel assembly and wheel bearing performance may be monitored. Further the condition of ancillary running gear may be ascertained; for example, the performance of suspension components may be determined from the behavior of unsprung masses in response to road stimuli in one embodiment.

Figure 3:
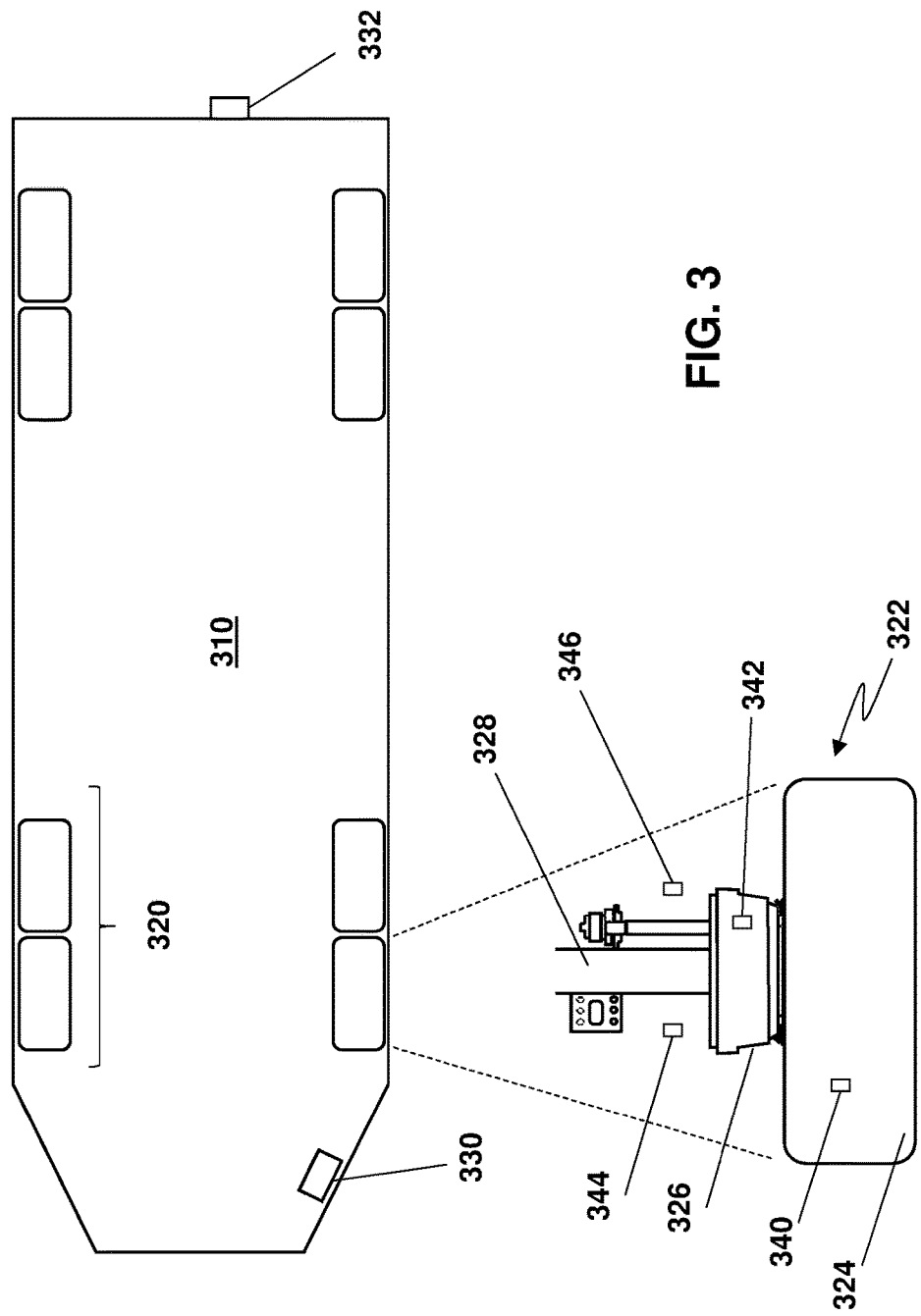
FIG. 3 is a block diagram of a trailer showing one wheel assembly in an expanded view.

For example, reference is now made to FIG. 3, which shows a schematic view of a trailer comprising a sensor system. In the embodiment of FIG. 3, a trailer 310 is shown having eight wheels 320. One wheel assembly 322 is expanded for visibility.

The wheel assembly 322 includes a tire 324, a bearing 326 and an axle 328.

The trailer 310 includes a sensor hub 330 which may collect data from sensors associated with the wheel assembly 322. The sensor hub 330 may then communicate in a wired or wireless fashion with a sensor gateway 332.

In some embodiments, sensors on wheel assembly 322 would communicate directly with sensor gateway 332 rather than through a sensor hub 330.

In accordance with the embodiment of FIG. 3, the wheel assembly 322 includes at least one TPMS sensor 340. The TPMS sensor 340 may measure and report the temperature and tire pressure within the tire or wheel assembly 322.

The wheel assembly 322 may further include a bearing sensor 342. For example, bearing sensor 342 may be a MEMS sensor used to measure acceleration and temperature of the wheel bearings.

Acoustic sensors 344 and 346 are also shown as part of wheel assembly 322. The acoustic sensors 344 and 346 may be placed in proximity to the various components that are being monitored. The acoustic sensors 344 and 346 measure sound emanating from the tires and/or wheel assembly and are therefore pressure wave sensors. In various embodiments, acoustic sensors 344 and 346 may include sensors to capture audible sound, sensors to capture ultrasonic sound, or sensors to capture both audible and ultrasonic sound.

In some cases, the acoustic sensors may be positioned and/or constructed to minimize environmental noise beyond what is being sensed. In particular, tire noise is representative of the road surface quality and may be retrieved from acoustic data collected on the wheel.

The tire noise may be collected and processed as follows. At least one acoustic sensor is coupled to each wheel or set of wheels at a location on the vehicle. Thereafter, the acoustic sensor collects data while the vehicle is in motion. The raw acoustic sensor data may be processed, for example in the frequency domain, to develop a characteristic signature over each sample period. Such conversion of raw acoustic sensor data may either occur on the vehicle, for example at the sensor, sensor hub or gateway, or may be passed as raw data to a server which may then process the data.

If the data conversion occurs at the trailer, the characteristic signature data may be aggregated prior to being transmitted to the servers in some embodiments.

The type, number and location of the sensors in FIG. 3 are however merely an example. In other embodiments, different types, number and locations of sensors may be provided.

Utilizing a system such as that described in FIG. 3, sensor data may be collected while a trailer or truck is in service. For example, such sensor data may be collected at predetermined intervals such as every five minutes. Alternatively, or in addition, the collection of data may be based on a trigger. A trigger may include the sensing of a sudden impact force such as a wheel passing over an irregular surface feature such as a pothole or a sudden change in environmental temperature such as when a vehicle may be driving into a snowstorm.

The sensor data may be collected, potentially aggregated or processed, and sent to a central server in one embodiment. The sending of the data may be supplemented with additional information, such as position/location of the vehicle, current operational parameters, together with identifying characteristics of the vehicle and its load.

The central server may then store and process the received sensor data and additional information.

Figure 4:
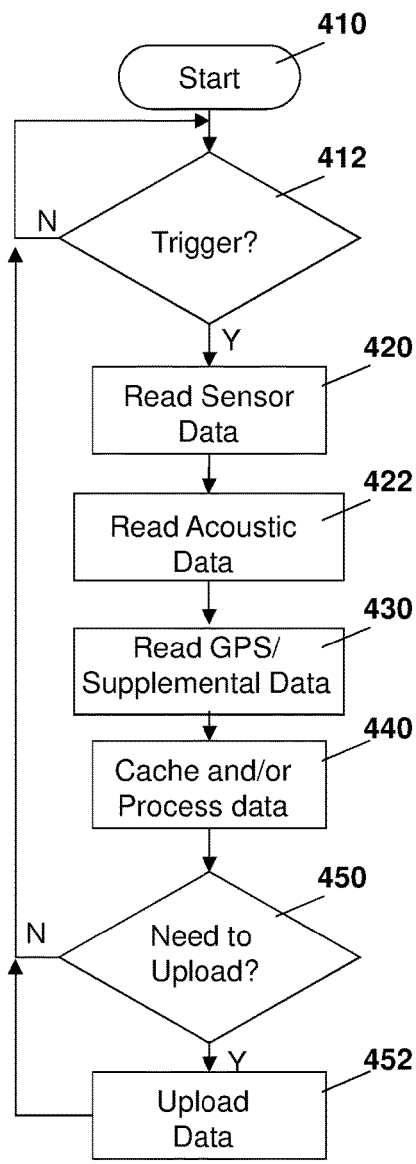
FIG. 4 is a process diagram showing a process at a sensor hub or gateway for providing sensor and supplemental data to a processing node.

For example, reference is now made to FIG. 4. In the embodiment of FIG. 4, the process starts at block 410 and proceeds to block 412 in which a check is made to determine whether a trigger condition has been met. As indicated above, the trigger condition may be a time condition. For example, sensor data may be collected every five minutes in some embodiments.

In other embodiments, the trigger at block 412 may be a high-impact condition or environmental condition. Other possibilities for a trigger 412 might include load conditions such as the deflection of a load bearing member or reaching a peak deflection threshold of a suspension component. A trigger 412 might also be generated on demand from a management system server or a manual request from a person such as a driver or rider in the vehicle. Other possibilities would also exist.

If a trigger condition is not met at the check at block 412, the process proceeds to loop back at block 412 until a trigger condition is met.

Once a trigger condition is met, the process proceeds from block 412 to block 420 in which sensor data is read. Such reading of the sensor data may, for example, occur at sensor modules or may be directly at the sensor gateway. If the reading is at sensor modules, the data may then be propagated to the sensor gateway through wireless or wired techniques as described above.

From block 420 the process proceeds to block 422 in which acoustic data may be read. Such acoustic data may, for example, come from acoustic sensors 344 or 346 in the embodiment of FIG. 3.

The acoustic data, read within block 422, may be stored or cached in a raw format or may be processed at a sensor module or a gateway prior to being uploaded to the server. The processing may include a frequency conversion or derivation, for example using a Fast Fourier Transform. The processing in the frequency domain may develop a characteristic signature over a sampling period, for example a trend. In this case, the characteristic signature data may be aggregated prior to being transmitted.

The process then proceeds to block 430, in which global positioning system (GPS) or other similar location/position information may be read and associated with the sensor data received at blocks 420 and/or 422. Further, in block 430, other supplemental data may be collected to supplement the sensor data and improve diagnostic capabilities in accordance with the embodiments described herein. For example, a timestamp or other identifying information may be attributed to the sensor data, environmental conditions or readings may be placed in association with sensor data, camera images may be associated with the sensor data, among other options.

Other sensor data that may be also be added includes brake wear sensors, or acoustic sensors that can detect brake anomalies, strain gauges among other options.

In still further embodiments, local system data may be collected from a vehicle data bus such as, for example, an On-Board Diagnostics (OBD) port to supplement the sensor data. Such data could include engine performance, vehicle speed, engine temperature, alarms or warnings generated by other vehicle subsystems, among other data.

As described below, supplemental information including GPS and mapping information may be used to provide intelligent processing of sensor information. For example, GPS location information may be used to determine the location of the truck, and may be used to find road conditions from a database. Different acoustic signatures may be experienced during travel on a dirt or gravel road rather than a paved road. Further, timestamp information along with GPS information may be used in processing to determine weather information for the vehicle. If the road is snow-covered or wet this may also provide different sensor readings.

The process then proceeds to block 440 in which the data is cached, and in some cases, may also be processed. The processing at block 440 may, for example, include the acoustic processing described above with regard to the frequency conversions to create characteristic signatures. Further, the processing may involve aggregating data or comparing the data to a baseline performance level. The baseline performance level may have been created by the manufacturer of the vehicle, by previous manual input, or from accumulated readings and data of the vehicle or similar vehicles within the fleet. Further, in some embodiments baseline performance data may be provided by a third party. The baseline may be stored locally within a component of the vehicle system or be stored on a server or in the cloud.

The processing may further include compression of the data for both storing the data at the sensor module or gateway, and further for transmitting the data to a server, as described below. The processed data may be compressed into a compressed form such as a signature or hash. It may also be filtered and a Fast Fourier Transform may be made to process the data and provide an analysis. Further, compression may involve correlation of information from different sensors or sensor modules.

The compressed raw sensor data may be then provided as a smaller data set that contains only useful information which may optimize memory chip sizes and minimize communication times.

Further, in some cases, the processing may use stored or historic information, or supplemental information.

In one embodiment, the processing may further comprise adding security to the data. For example, the data may be signed or encrypted to ensure the authenticity of the data.

From block 440 the process proceeds to block 450 in which a check is made to determine whether the data needs to be uploaded. For example, the data may be uploaded every six sampling periods in some embodiments. In other cases, data is not uploaded until the vehicle is stationary. In other cases, the data may only be uploaded in certain geographic areas. In other cases, the data is uploaded at every sampling cycle. Other examples are possible.

From block 450, if the data needs to be uploaded then the process proceeds to block 452 in which the data is uploaded to a server.

From block 450 if data does not need to be uploaded, or from block 452, the process returns to block 412 in which the process awaits the next trigger condition.

Once the sensor data is collected, it may be processed. The processing may occur, in some embodiments, at the sensor module or gateway. However, in other embodiments the sensor processing may be done, at least partially, on the server side. The entity performing such processing is referred to herein as the processing node.

Figure 5:
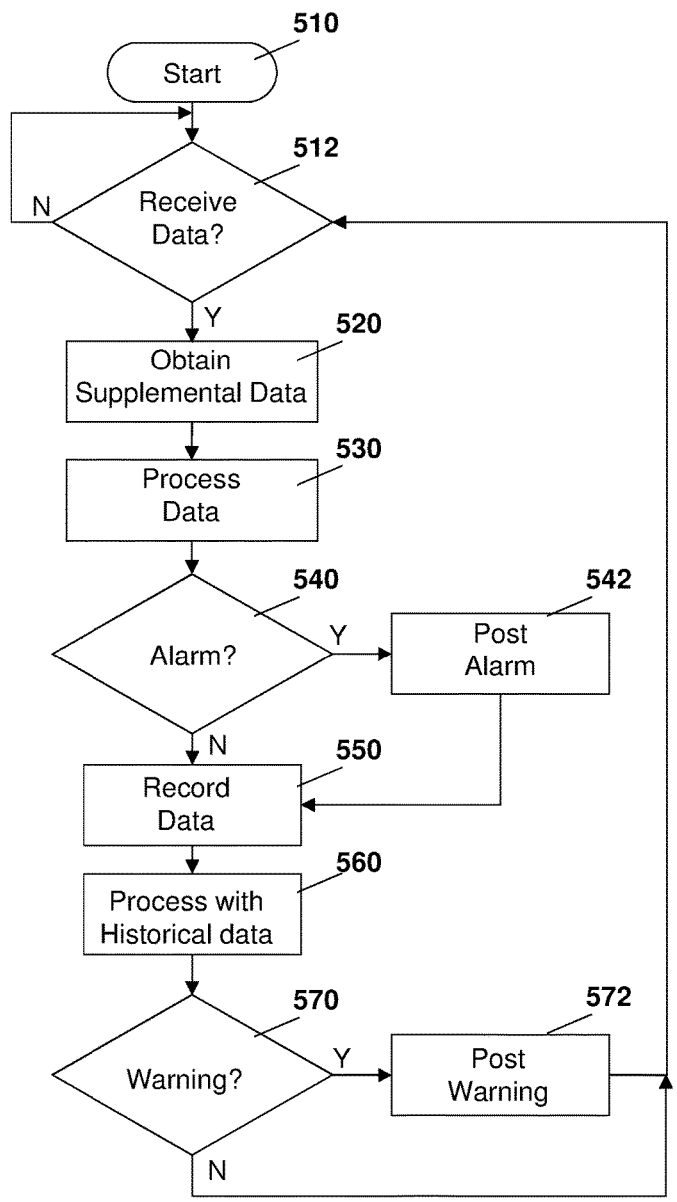
FIG. 5 is a process diagram showing a process at a processing node for processing sensor and supplemental data.

Reference now made to FIG. 5, which shows a process for the analysis of received data. In particular, the process of FIG. 5 starts at block 510 and proceeds to block 512 in which check is made to determine whether sensor data has been received. If not, the process continues to loop at block 512 until sensor data is received.

Once sensor data is received, the process proceeds from block 512 to block 520 in which supplemental data related to the received data is obtained. For example, if the received data includes a GPS fix (location/position information), the supplemental data obtained at block 520 may include the weather conditions for the particular time and location that the sensor data was obtained. It may further include map information including a roadway description. It may further include historic data obtained from either this particular vehicle or from other vehicles that have travelled on the same roadway. Other examples of supplemental data are possible.

The data at block 512 and the supplemental data at block 520 may be collected for a duration of a trip or across multiple trips in some embodiments.

Based on the data received at block 512 and supplemental data at block 520, processing may then occur. The data is processed at block 530 in the embodiment of FIG. 5.

For example, as provided above, TPMS sensor data received at block 512 may be used to monitor the state of each of the tires. The air volume in a tire is related to a ratio of temperature and pressure. If the tire is not losing air, the ratio should remain constant. If the ratio changes over time, this could relate to air pressure loss in the tire. Comparing information between adjacent wheels may allow the detection of uneven tire wear.

Similarly, bearing sensors could record temperature and vibration representing roughness or wear in the wheel bearings. Sensor measurements that show increased temperature or vibration beyond the normal operation could trigger the system to alert an operator.

Acoustic sensors could record the sound of the wheel assembly and derive a characteristic signature over a sampling interval. For example, a sampling interval may be in the order of 10 to 20 seconds. In this case, a characteristic signature based on an analysis of the acoustic input in the frequency domain could be developed.

In some embodiments, an acoustic base line may be created, for example, using a vehicle that is known to be in good condition. Such acoustic base line may then be used for processing of acoustic signals. However, as described above, in other embodiments the base line could be acquired in different ways.

The processing could, in some embodiments, consider the status of other wheel assemblies. Thus, if bearing sensors at one wheel assembly are providing higher temperature or vibration readings, this may indicate that the bearing may be at risk of failure, for example.

The processing could consider supplemental information, either associated with the data received at block 512 or obtained at block 520.

For example, in one embodiment the supplemental data received at block 512 could include a location/position fix and a timestamp. Based on this information, weather conditions for the location of the vehicle (trailer) could be determined at block 520. Such weather conditions could indicate that the temperature in the area of the vehicle was extremely cold, and this could be used in conjunction with the TPMS readings.

In other embodiments, the supplemental data received at block 512 could be a position/location fix for the vehicle (trailer). Such a position/location fix could then be used at block 520 to determine that a stretch of road is being repaved and thus the acoustic information received at block 512 should consider the altered road noise.

In still further embodiments, the supplemental information could include a camera picture showing a snow-covered roadway. Image processing at block 530 could then use the image data for processing the sensor data. Other options are possible.

In some embodiments, other supplemental data can also be used. For example, if the trailer is carrying a load of animals, such information may be provided to the processing node and the noise generated by such animals may also be filtered out. Other examples of filtering using supplemental data are also possible.

In other embodiments, supplemental data can include load information. For example, information from sensors such as a strain gage sensor on the suspension or a sensor on an air suspension component may provide information regarding the load, which may then allow factors that affect wheel assembly performance, such as unbalanced load, to be factored into the processing at block 530.

The processing at block 530 may provide for alarm conditions if a component is on the verge of failure. Therefore, the process proceeds to block 540 and checks whether an alarm condition exists. If yes, the alarm condition may be posted at block 542. Such posting may include alerting an operator of the vehicle, a transportation company, other drivers within the company and other drivers of vehicles within the vicinity, among other users of the system.

The alarm at block 542 could be categorized into various levels. For example, the alarm could indicate to a user to stop the vehicle immediately. In other cases, the alarm could indicate that the vehicle should stop in a certain time period or a certain distance. For example, the data may indicate that the vehicle should stop in the next 10,000 km, within the next 10 km, or immediately.

From block 540 if an alarm condition does not exist, or from block 542, the process may then proceed to block 550 in which the data is recorded and stored.

The process may then proceed to block 560 in which the recorded data is processed with regard to historic data. The processing at block 560 may look for trends over time that may lead to failure of a vehicle's bearings or tires. Further, the data may be aggregated from many vehicles to better predict maintenance and failure conditions. Such predictions can be used to schedule future maintenance appointments within the fleet management server/system, or by sending data to an external server/system.

Further, the ability to process the data from multiple sensors to define and calibrate the behavior for normal operations and use supplemental data to better predict anomalous conditions and trends allows for better prediction of the failure of the wheel assembly, bearing or tire.

The comparison of the sensor data with historical data may allow for preventative maintenance to occur, rather than a failure. The comparison of sensor data with historical data also allows the system to automatically detect when maintenance has occurred or parts replaced due to sudden better data. Data that maintenance has occurred may also be input manually and used to reset or restart trend analysis from that point in time.

The historical processing at block 560 could create a warning condition to warn an operator to inspect their vehicle after the completion of the trip. This is shown for example with block 570 in which a check is made to determine whether warning exists and if yes, the process proceeds to block 572 in which the warning is posted to the operator, for example.

From block 570 or block 572 the process then proceeds back to block 512 in which new data from sensors is potentially received.

The processing at blocks 530 and 560 could utilize templates to allow for better processing. Such templates could be developed to allow for the identification that not only a change in the performance of the bearing or tire has occurred, but it could categorize the nature of the change. For example, in some cases, the readings of the tires and bearings could indicate that a load has shifted and this may lead to failure prediction.

In accordance with the above, the use of the historic data as well as the current data may provide for component failure prediction, which may allow for scheduled maintenance rather than unscheduled maintenance on component failure. This is typically cheaper in the transport industry. The historic data may also be used to determine if potential failure predictions from the current data are in themselves anomalous and only require a cursory check or the re-setting of a false sensor trigger.

A server performing the processing of FIG. 5 may be a server such as server 240 or 242. Such server may be any network node. For example, one simplified server that may perform the embodiments described above is provided with regards to FIG. 6.

Figure 6:
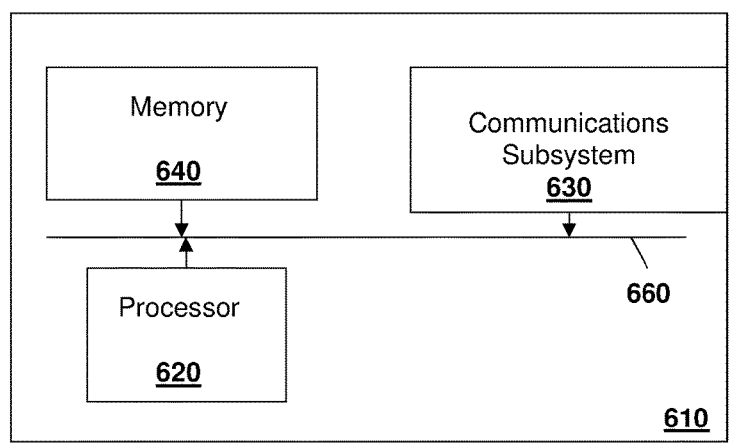
FIG. 6 is a block diagram of an example computing device capable of being used in accordance with the embodiments of the present disclosure.

In FIG. 6, server 610 includes a processor 620 and a communications subsystem 630, where the processor 620 and communications subsystem 630 cooperate to perform the methods of the embodiments described herein.

The processor 620 is configured to execute programmable logic, which may be stored, along with data, on the server 610, and is shown in the example of FIG. 6 as memory 640.

The memory 640 can be any tangible, non-transitory computer readable storage medium, such as optical (e.g., CD, DVD, etc.), magnetic (e.g., tape), flash drive, hard drive, or other memory known in the art. In one embodiment, processor 620 may also be implemented entirely in hardware and not require any stored program to execute logic functions.

Alternatively, or in addition to the memory 640, the server 610 may access data or programmable logic from an external storage medium, for example through the communications subsystem 630.

The communications subsystem 630 allows the server 610 to communicate with other devices or network elements.

Communications between the various elements of the server 610 may be through an internal bus 660 in one embodiment. However, other forms of communication are possible.

The embodiments described herein are examples of structures, systems or methods having elements corresponding to elements of the techniques of this application. This written description may enable those skilled in the art to make and use embodiments having alternative elements that likewise correspond to the elements of the techniques of this application. The intended scope of the techniques of this application thus includes other structures, systems or methods that do not differ from the techniques of this application as described herein, and further includes other structures, systems or methods with insubstantial differences from the techniques of this application as described herein.

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be employed. Moreover, the separation of various system components in the implementation descried above should not be understood as requiring such separation in all implementations, and it should be understood that the described program components and systems can generally be integrated together in a signal software product or packaged into multiple software products. In some cases, functions may be performed entirely in hardware and such a solution may be the functional equivalent of a software solution Also, techniques, systems, subsystems, and methods described and illustrated in the various implementations as discrete or separate may be combined or integrated with other systems, modules, techniques, or methods. Other items shown or discussed as coupled or directly coupled or communicating with each other may be indirectly coupled or communicating through some interface, device, or intermediate component, whether electrically, mechanically, or otherwise. Other examples of changes, substitutions, and alterations are ascertainable by one skilled in the art and may be made.

While the above detailed description has shown, described, and pointed out the fundamental novel features of the disclosure as applied to various implementations, it will be understood that various omissions, substitutions, and changes in the form and details of the system illustrated may be made by those skilled in the art. In addition, the order of method steps is not implied by the order they appear in the claims.

When messages are sent to/from an electronic device, such operations may not be immediate or from the server directly. They may be synchronously or asynchronously delivered, from a server or other computing system infrastructure supporting the devices/methods/systems described herein. The foregoing steps may include, in whole or in part, synchronous/asynchronous communications to/from the device/infrastructure. Moreover, communication from the electronic device may be to one or more endpoints on a network. These endpoints may be serviced by a server, a distributed computing system, a stream processor, etc. Content Delivery Networks (CDNs) may also provide may provide communication to an electronic device. For example, rather than a typical server response, the server may also provision or indicate a data for content delivery network (CDN) to await download by the electronic device at a later time, such as a subsequent activity of electronic device. Thus, data may be sent directly from the server, or other infrastructure, such as a distributed infrastructure, or a CDN, as part of or separate from the system.

Typically, storage mediums can include any or some combination of the following: a semiconductor memory device such as a dynamic or static random access memory (a DRAM or SRAM), an erasable and programmable read-only memory (EPROM), an electrically erasable and programmable read-only memory (EEPROM) and flash memory; a magnetic disk such as a fixed, floppy and removable disk; another magnetic medium including tape; an optical medium such as a compact disk (CD) or a digital video disk (DVD); or another type of storage device. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In the foregoing description, numerous details are set forth to provide an understanding of the subject disclosed herein. However, implementations may be practiced without some of these details. Other implementations may include modifications and variations from the details discussed above. It is intended that the appended claims cover such modifications and variations.

The invention claimed is:

1. A method for monitoring performance of at least one component on a moving platform, the method comprising:
receiving sensor data for the at least one component, along with supplemental data, at a processing node; and
processing the sensor data, the processing using the supplemental data to filter the sensor data;
wherein the supplemental data comprises at least one of: a location fix, a time stamp, an image from a camera on the moving platform, a temperature, a pressure, weather conditions, map information, historic data from the moving platform, historic data from a different moving platform, or load information.

2. The method of claim 1, wherein the at least one component is a wheel assembly, and wherein the sensor data comprises data from at least one of: a bearing sensor; a tire pressure monitoring sensor; or an acoustic sensor.

3. The method of claim 2, wherein sensor data from the acoustic sensor is processed in the frequency domain to develop a characteristic signature.

4. The method of claim 3, wherein the processing comprises comparing the characteristic signature against a baseline characteristic signature.

5. The method of claim 2, wherein sensor data from the bearing sensor includes at least one of vibration or temperature data.

6. The method of claim 5, wherein the processing comprises comparing sensor data from the wheel assembly with sensor data from at least one other wheel assembly on the moving platform.

7. The method of claim 2, wherein the supplemental data includes a location fix and a timestamp, and wherein the processing comprises:
retrieving weather conditions based on the location fix and timestamp; and filtering the sensor data based on the weather conditions.

8. The method of claim 2, wherein the supplemental data includes a position fix, and wherein the processing comprises:
retrieving road information based on the position fix; and
filtering the sensor data based on the road information.

9. The method of claim 2, wherein the supplemental data is an image from a camera on the moving platform, and wherein the processing comprises:
performing image processing to determine road conditions; and
filtering the sensor data based on the determined road conditions.

10. The method of claim 2, further comprising using historical data from at least one of the moving platform or a fleet of moving platforms to further process the sensor data.

11. A processing node for monitoring performance of at least one component on a moving platform, the processing node comprising:
a processor; and
a communications subsystem,
wherein the processing node is configured to:
receive sensor data for the at least one component, along with supplemental data; and
process the sensor data, the processing using the supplemental data to filter the sensor data;
wherein the supplemental data comprises at least one of: a location fix, a time stamp, an image from a camera on the moving platform, a temperature, a pressure, weather conditions, map information, historic data from the moving platform, historic data from a different moving platform, or load information.

12. The processing node of claim 11, wherein the at least one component is a wheel assembly, and wherein the sensor data comprises data from at least one of: a bearing sensor; a tire pressure monitoring sensor; or an acoustic sensor.

13. The processing node of claim 12, wherein sensor data from the acoustic sensor is processed in the frequency domain to develop a characteristic signature.

14. The processing node of claim 13, wherein the processing node is configured to process by comparing the characteristic signature against a baseline characteristic signature.

15. The processing node of claim 12, wherein sensor data from the bearing sensor includes at least one of vibration or temperature data.

16. The processing node of claim 15, wherein the processing node is configured to process by comparing sensor data from the wheel assembly with sensor data from at least one other wheel assembly on the moving platform.

17. The processing node of claim 12, wherein the supplemental data includes a location fix and a timestamp, and wherein the processing node is configured to process by:
retrieving weather conditions based on the location fix and timestamp; and
filtering the sensor data based on the weather conditions.

18. The processing node of claim 12, wherein the supplemental data includes a position fix, and wherein the processing node is configured to process by:
retrieving road information based on the position fix; and
filtering the sensor data based on the road information.

19. The processing node of claim 12, wherein the supplemental data is an image from a camera on the moving platform, and wherein the processing node is configured to process by:
performing image processing to determine road conditions; and
filtering the sensor data based on the determined road conditions.

20. The processing node of claim 12, wherein the processing node is further configured to use historical data from at least one of the moving platform or a fleet of moving platforms to further process the sensor data.

21. A computer readable medium for storing instruction code, which, when executed by a processor on a processing node are configured for monitoring performance of at least one component on a moving platform, the instruction code causing the processing node to:
receive sensor data for the at least one component, along with supplemental data; and
process the sensor data, the processing using the supplemental data to filter the sensor data;
wherein the supplemental data comprises at least one of:
a location fix, a time stamp, an image from a camera on the moving platform, a temperature, a pressure, weather conditions, map information, historic data from the moving platform, historic data from a different moving platform, or load information.

* * * * *